(12) United States Patent
Lee et al.

(10) Patent No.: US 10,898,703 B2
(45) Date of Patent: Jan. 26, 2021

(54) MICRONEEDLE TEMPLATE AND MICRONEEDLE PREPARED USING THE SAME

(71) Applicant: S-SKIN. CO., LTD., Suwon-si (KR)

(72) Inventors: Jeong Gun Lee, Seoul (KR); Shin Hee Cho, Suwon-si (KR); Bo Young Shin, Suwon-si (KR)

(73) Assignee: S-SKIN. CO., LTD., Suwon-Si (KR)

( * ) Notice: Subject to any disclaimer, the term of this patent is extended or adjusted under 35 U.S.C. 154(b) by 0 days.

(21) Appl. No.: 16/553,690

(22) Filed: Aug. 28, 2019

(65) Prior Publication Data

US 2020/0009363 A1  Jan. 9, 2020

Related U.S. Application Data

(63) Continuation of application No. PCT/KR2018/001421, filed on Feb. 2, 2018.

(30) Foreign Application Priority Data

Sep. 8, 2017 (KR) .................. 10-2017-0115302

(51) Int. Cl.
*A61M 37/00* (2006.01)
*B29C 33/38* (2006.01)
*A61B 5/15* (2006.01)
*B29L 31/00* (2006.01)

(52) U.S. Cl.
CPC ..... *A61M 37/0015* (2013.01); *B29C 33/3842* (2013.01); *A61B 5/150984* (2013.01); *A61M 2037/0023* (2013.01); *A61M 2037/0046* (2013.01); *A61M 2037/0053* (2013.01); *A61M 2207/10* (2013.01); *B29K 2907/045* (2013.01);
(Continued)

(58) Field of Classification Search
CPC .................. A61M 2037/0053; B29C 33/3842
See application file for complete search history.

(56) References Cited

U.S. PATENT DOCUMENTS

2006/0202385 A1* 9/2006 Xu .................... A61M 37/0015
                                                                     264/219
2007/0191761 A1   8/2007 Boone et al.
2009/0162798 A1   6/2009 Tomono
(Continued)

FOREIGN PATENT DOCUMENTS

JP        2016529115 A     9/2016
KR   10-2011-0022554 A     3/2011
(Continued)

OTHER PUBLICATIONS

International Search Report (English); International Patent Application No. PCT/KR2018/001421, dated May 23, 2018 (2 pages).
(Continued)

*Primary Examiner* — Galen H Hauth
(74) *Attorney, Agent, or Firm* — Hamre, Schumann, Mueller & Larson, P.C.

(57) ABSTRACT

Provided are a microneedle template including: a substrate on which at least one microneedle shapes are formed; and a diamond layer formed on the surface of the at least one microneedle shapes, a method for preparing the microneedle template, a microneedle prepared using the microneedle template, and a method for preparing the microneedle.

11 Claims, 10 Drawing Sheets

(52) U.S. Cl.
CPC ..... *B29K 2909/04* (2013.01); *B29L 2031/756* (2013.01); *B29L 2031/7544* (2013.01)

(56) References Cited

U.S. PATENT DOCUMENTS

2010/0305516 A1* 12/2010 Xu .................... A61M 37/0015
604/272
2015/0094648 A1* 4/2015 Toyohara ............. A61K 9/0021
604/46

FOREIGN PATENT DOCUMENTS

| KR | 10-2011-0086248 A | 7/2011 |
| KR | 10-1383285 B1 | 4/2014 |
| KR | 10-2017-0061042 A | 6/2017 |
| WO | 2016183435 A1 | 11/2016 |

OTHER PUBLICATIONS

Notice of Allowance, Korean Patent Application No. 10-2017-0115302, dated Aug. 9, 2019, with English translation (4 pages).
Final Rejection, Korean Patent Application No. 10-2017-0115302, dated Jun. 27, 2019, with English translation (9 pages).
Notice of Preliminary Rejection, Korean Patent Application 10-2017-0115302, with English translation (16 pages).

* cited by examiner

MAXIMUM LENGTH OF DIAGONAL LINE OF HEXAGONAL CROSS SECTION

MAXIMUM LENGTH OF DIAGONAL LINE OF TETRAGONAL CROSS SECTION

MICRONEEDLE TEMPLATE AND MICRONEEDLE PREPARED USING THE SAME

CROSS-REFERENCE TO RELATED APPLICATIONS

This application is a continuation of PCT Application No. PCT/KR2018/001421, filed on Feb. 2, 2018, which claims priority to Korean Patent Application No. 10-2017-0115302, filed on Sep. 8, 2017, both of which are hereby incorporated by references in their entirety.

TECHNICAL FIELD

The present disclosure relates to a microneedle template including: a substrate on which at least one microneedle shapes is formed; and a diamond layer formed on the surface of the at least one microneedle shapes, a method for preparing the microneedle template, a microneedle prepared using the microneedle template, and a method for preparing the microneedle.

BACKGROUND

A drug delivery system (DDS) refers to a series of techniques for controlling the delivery of materials having pharmacological activity to cells, tissues, and organs using various physicochemical techniques. The most common drug delivery system is an oral drug intake. In addition, there is a transdermal drug delivery system that can be topically applicable, etc. As such, a metallic syringe has been used for at least 150 years to inject a liquid-phase drug by penetrating the epidermis, but there have been disadvantages such as causing pain, temporary drug injection, and needle phobia. To improve the way of drug injection using a syringe, a microscale transdermal microneedle which is much smaller than a syringe has been developed and used.

In general, a microneedle is a device for injecting a skin care material or a drug into the skin tissue or extracting a body fluid such as blood from the inside of the skin. The microneedle can topically and continuously inject a drug and can also minimize pain on insertion into the skin so that the use of microneedles has been rapidly increased in various fields recently.

One of various methods for preparing microneedles is to use a microneedle array mold for preparing microneedles. The microneedle array mold is typically formed of silicon and thus is weak in hardness and strength and has an uneven surface.

Korean Patent No. 10-1383285 discloses "a method of manufacturing solid solution perforator patches and uses thereof".

DISCLOSURE OF THE INVENTION

Problems to be Solved by the Invention

The present disclosure provides: a microneedle template including a substrate on which at least one microneedle shapes is formed and a diamond layer formed on the surface of the at least one microneedle shapes; a method for preparing the microneedle template; a microneedle prepared using the microneedle template; and a method for preparing the microneedle.

However, problems to be solved by the present disclosure are not limited to the above-described problems. Although not described herein, other problems to be solved by the present disclosure can be clearly understood by a person with ordinary skill in the art from the following description.

Means for Solving the Problems

A first aspect of the present disclosure provides a microneedle template, including: a substrate on which at least one microneedle shapes is formed; and a diamond layer formed on the surface of the at least one microneedle shapes.

A second aspect of the present disclosure provides a method for preparing a microneedle template, including: forming at least one microneedle shapes on a substrate; and forming a diamond layer on the surface of the at least one microneedle shapes.

A third aspect of the present disclosure provides a method for preparing a microneedle, including: forming a negative mold using the microneedle template according to the first aspect of the present disclosure; and adding a microneedle-forming material to the negative mold and removing the negative mold to obtain a microneedle.

A fourth aspect of the present disclosure provides a microneedle, prepared using the microneedle template according to the first aspect of the present disclosure.

Effects of the Invention

According to embodiments of the present disclosure, a microneedle template has excellent stability and thus is suitable for mass production of microneedles. Further, according to embodiments of the present disclosure, the microneedle template has high evenness and thus can be used properly for preparation of microneedles having high uniformity.

According to embodiments of the present disclosure, a method for preparing a microneedle has the advantage to reduce manufacturing costs compared to the conventional methods for preparing a microneedle using a silicon microneedle array and a photolithography method.

According to embodiments of the present disclosure, a microneedle prepared using the microneedle template has high uniformity, which may result in the improvement of skin penetration of a material contained in the microneedle.

According to embodiments of the present disclosure, the microneedle prepared using the microneedle template has high skin penetration and thus can efficiently deliver a material.

According to embodiments of the present disclosure, the microneedle template has higher strength than the conventional microneedle templates and thus can be used semipermanently for preparing a plurality of negative molds.

BEST MODE FOR CARRYING OUT THE INVENTION

Figure 1:
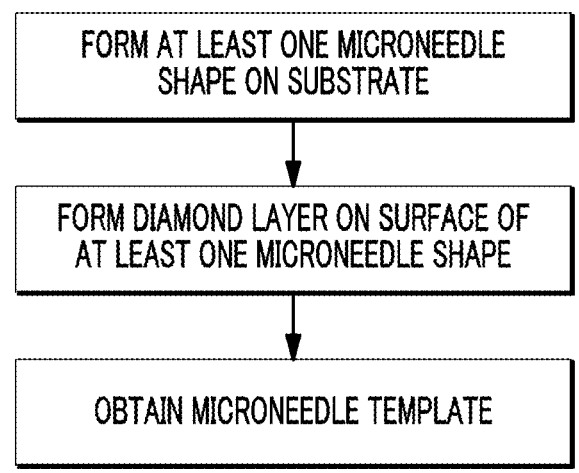
FIG. 1 is a schematic illustration of a method for preparing a microneedle template according to an embodiment of the present disclosure.
Figure 2:
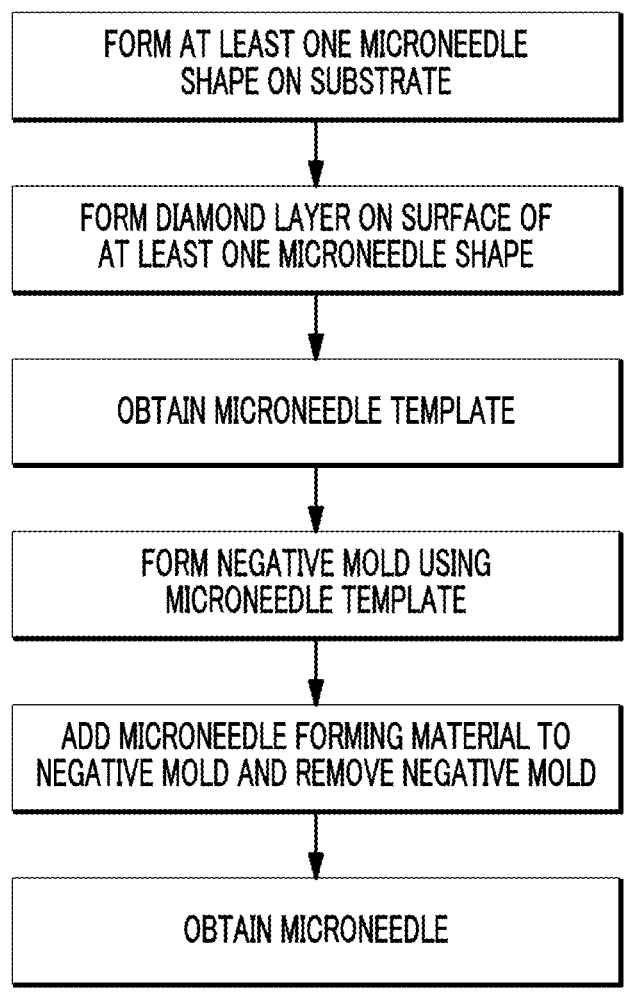
FIG. 2 is a schematic illustration of a method for preparing a microneedle using the microneedle template according to an embodiment of the present disclosure.

Hereafter, examples will be described in detail with reference to the accompanying drawings so that the present disclosure may be readily implemented by those skilled in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "microneedle template" refers to a positive mold or a positive cast for preparing a microneedle and is used in the same meaning as "microneedle master".

Hereinafter, embodiments of the present disclosure will be described in detail, but the present disclosure may not be limited thereto.

A first aspect of the present disclosure provides a microneedle template, including: a substrate on which at least one microneedle shapes is formed; and a diamond layer formed on the surface of the at least one microneedle shapes.

In an embodiment of the present disclosure, the substrate on which the at least one microneedle shapes is formed may include one selected from the group consisting of a metal, a semimetal, an alloy, a semimetal compound, a metal compound, and combinations thereof.

In an embodiment of the present disclosure, the metal may include one selected from the group consisting of tungsten, titanium, molybdenum, niobium, tantalum, chromium, and combinations thereof, but may not be limited thereto.

In an embodiment of the present disclosure, the semimetal may include one selected from the group consisting of silicon, germanium, arsenic, antimony, tellurium, polonium, and combinations thereof, but may not be limited thereto.

In an embodiment of the present disclosure, the alloy may include an ultrahard alloy, and the ultrahard alloy may include one selected from the group consisting of the combinations of carbides of metals in Groups IVB, VB, VIB of the Periodic Table of Elements, such as WC, TiC, MoC, NbC, TaC, $Cr_3C_2$, and the like, but may not be limited thereto.

In an embodiment of the present disclosure, the ultrahard alloy may be given electrical conductivity by using a palladium catalyst, but may not be limited thereto. When the electrical conductivity is given using the palladium catalyst, well-known materials such as a conduction agent used for plating on an ABS resin or the like may be used. However, the present disclosure may not be limited thereto.

In an embodiment of the present disclosure, the semimetal compound may include one selected from the group consisting of a silicon nitride, a silicon carbide, silicon oxide, and combinations thereof, but may not be limited thereto. Ceramics including the silicon nitride, the silicon carbide, the silicon oxide, and the like have excellent thermal shock resistance and high rupture resistance and thus can improve processability and durability such as thermal resistance and wear resistance of the microneedle template. Therefore, the microneedle template according to an embodiment of the present disclosure can be used properly for mass production of microneedles.

In an embodiment of the present disclosure, the metal compound may include a compound of the metal, but may not be limited thereto. The metal compound may include, for example, one selected from the group consisting of an oxide, a nitride, a carbide, an oxynitride and a carbonitride of the metal, and combinations thereof, but may not be limited thereto.

In an embodiment of the present disclosure, WC has a high melting point of about 2,870° C. and thus may have high thermal resistance and also exhibit excellent wear resistance and compression strength, but may not be limited thereto. For example, the WC has the Mohs hardness of from 9 to 9.5 and the Vickers hardness of from about 1,700 to about 2,400.

In an embodiment of the present disclosure, when the substrate on which the at least one microneedle shapes is formed includes WC, the microneedle template can be improved in durability such as thermal resistance and wear resistance and thus can be used properly for mass production of microneedles, but may not be limited thereto.

In an embodiment of the present disclosure, the WC may have the specific gravity of from about 13 g/cm$^3$ to about 15 g/cm$^3$, from about 13.5 g/cm$^3$ to about 15 g/cm$^3$, from about 14 g/cm$^3$ to about 15 g/cm$^3$, from about 14.5 g/cm$^3$ to about 15 g/cm$^3$, from about 13 g/cm$^3$ to about 14.5 g/cm$^3$, from about 13 g/cm$^3$ to about 14 g/cm$^3$, or from about 13 g/cm$^3$ to about 13.5 g/cm$^3$, but may not be limited thereto. For example, when the WC has the specific gravity in the above-described range, the microneedle template can be improved in durability such as thermal resistance and wear resistance and thus can be used properly for mass production of microneedles, but may not be limited thereto.

In an embodiment of the present disclosure, the WC may have the hardness of from about 85 HRA to about 95 HRA, from about 87 HRA to about 95 HRA, from about 89 HRA to about 95 HRA, from about 91 HRA to about 95 HRA, from about 93 HRA to about 95 HRA, from about 85 HRA to about 93 HRA, from about 85 HRA to about 91 HRA, from about 85 HRA to about 89 HRA, or from about 85 HRA to about 87 HRA, but may not be limited thereto. For example, when the WC has the hardness in the above-described range, the microneedle template can be improved in durability such as thermal resistance and wear resistance and thus can be used properly for mass production of microneedles, but may not be limited thereto.

In an embodiment of the present disclosure, the WC may have the flexural strength of from about 260 kgf/mm$^2$ to about 355 kgf/mm$^2$, from about 260 kgf/mm$^2$ to about 335 kgf/mm$^2$, from about 260 kgf/mm$^2$ to about 315 kgf/mm$^2$, from about 260 kgf/mm$^2$ to about 295 kgf/mm$^2$, from about 260 kgf/mm$^2$ to about 275 kgf/mm$^2$, from about 280 kgf/mm$^2$ to about 355 kgf/mm$^2$, from about 300 kgf/mm$^2$ to about 355 kgf/mm$^2$, from about 320 kgf/mm$^2$ to about 355 kgf/mm$^2$, or from about 340 kgf/mm$^2$ to about 355 kgf/mm$^2$, but may not be limited thereto. For example, when the WC has the flexural strength in the above-described range, the microneedle template can be improved in durability such as thermal resistance and wear resistance and thus can be used properly for mass production of microneedles, but may not be limited thereto.

In an embodiment of the present disclosure, the diamond layer may have a density of from about 3.4 g/cm$^3$ to about 3.7 g/cm$^3$, from about 3.45 g/cm$^3$ to about 3.7 g/cm$^3$, from about 3.5 g/cm$^3$ to about 3.7 g/cm$^3$, from about 3.55 g/cm$^3$ to about 3.7 g/cm$^3$, from about 3.6 g/cm$^3$ to about 3.7 g/cm$^3$, from about 3.65 g/cm$^3$ to about 3.7 g/cm$^3$, from about 3.4 g/cm$^3$ to about 3.65 g/cm$^3$, from about 3.4 g/cm$^3$ to about 3.6 g/cm$^3$, from about 3.4 g/cm$^3$ to about 3.55 g/cm$^3$, from about 3.4 g/cm$^3$ to about 3.5 g/cm$^3$, or from about 3.4 g/cm$^3$ to about 3.45 g/cm$^3$, but may not be limited thereto. For example, when the diamond layer has the density in the above-described range, the microneedle template can be improved in durability such as thermal resistance and wear resistance and thus can be used properly for mass production of microneedles, but may not be limited thereto.

In an embodiment of the present disclosure, the diamond layer may have the hardness of from about 60 Gpa to about 120 Gpa, from about 70 Gpa to about 120 Gpa, from about 80 Gpa to about 120 Gpa, from about 90 Gpa to about 120 Gpa, from about 100 Gpa to about 120 Gpa, from about 110 Gpa to about 120 Gpa, from about 60 Gpa to about 110 Gpa, from about 60 Gpa to about 100 Gpa, from about 60 Gpa to about 90 Gpa, from about 60 Gpa to about 80 Gpa, or from about 60 Gpa to about 70 Gpa, but may not be limited thereto. For example, when the diamond layer has the hardness in the above-described range, the microneedle template can be improved in durability such as thermal resistance and wear resistance and thus can be used properly for mass production of microneedles, but may not be limited thereto.

In an embodiment of the present disclosure, the diamond layer may have the elastic modulus of from about 800 Gpa to about 1,000 Gpa, from about 850 Gpa to about 1,000 Gpa, from about 900 Gpa to about 1,000 Gpa, from about 950 Gpa to about 1,000 Gpa, from about 800 Gpa to about 950 Gpa, from about 800 Gpa to about 900 Gpa, or from about 800 Gpa to about 850 Gpa, but may not be limited thereto. For example, when the diamond layer has the elastic modulus in the above-described range, the microneedle template can be improved in durability such as thermal resistance and wear resistance and thus can be used properly for mass production of microneedles, but may not be limited thereto.

In an embodiment of the present disclosure, the diamond layer may have the refractive index of from about 2.3 to about 2.5, from about 2.35 to about 2.5, from about 2.4 to about 2.5, from about 2.45 to about 2.5, from about 2.3 to about 2.45, from about 2.3 to about 2.4, or from about 2.3 to about 2.35, but may not be limited thereto. For example, when the diamond layer has the refractive index in the above-described range, the microneedle template can be improved in durability such as thermal resistance and wear resistance and thus can be used properly for mass production of microneedles, but may not be limited thereto.

In an embodiment of the present disclosure, the diamond layer may have the resistivity of about $10^6$ or more, but may not be limited thereto.

In an embodiment of the present disclosure, the thickness of the diamond layer may be about 10 μm or less, from about 1 μm to about 10 μm, from about 3 μm to about 10 μm, from about 5 μm to about 10 μm, from about 7 μm to about 10 μm, from about 1 μm to about 9 μm, from about 1 μm to about 7 μm, from about 1 μm to about 5 μm, or from about 1 μm to about 3 μm, but may not be limited thereto.

In an embodiment of the present disclosure, when the diamond layer has the thickness of less than about 1 μm, it is difficult to accurately control the thickness of a coating of the diamond layer and a problem may occur that the coating of the diamond layer may be easily peeled off.

In an embodiment of the present disclosure, when the diamond layer has the thickness of more than about 10 μm, the point of a microneedle prepared using the microneedle template may be blunt, and thus the skin penetration may decrease and the manufacturing costs of microneedle templates and microneedles may increase.

In an embodiment of the present disclosure, the diamond layer may be formed by a chemical vapor deposition method or an atomic layer deposition method, but may not be limited thereto. The chemical vapor deposition method may include, for example, a chemical vapor deposition method using DC plasma, a chemical vapor deposition method using RF plasma, a chemical vapor deposition method using a hot filament, a chemical vapor deposition method using microwave plasma, and a chemical vapor deposition method using electron cyclotron resonance (ECR) plasma, but may not be limited thereto.

In an embodiment of the present disclosure, the diamond layer may be deposited by the chemical vapor deposition method using a hot filament having a temperature of about 2,000° C., but may not be limited thereto.

In an embodiment of the present disclosure, the diamond layer may make the microneedle template more uniformly by coating uneven surfaces formed during a grinding process of the substrate on which the at least one microneedle shapes are formed, but may not be limited thereto.

In an embodiment of the present disclosure, the diamond layer may be formed on the surface of the microneedle shape and thus can decrease the unevenness of the surface of the microneedle shape and increase the wear resistance thereof. However, the present disclosure may not be limited thereto.

In an embodiment of the present disclosure, the length of the microneedle shape needs to be suitable to penetrate the stratum corneum of the skin and reach the epidermal layer or dermal layer under the stratum corneum and may be, for example, about 2,000 µm or less, from about 10 µm to about 2,000 µm, from about 150 µm to about 2,000 µm, from about 250 µm to about 2,000 µm, from about 350 µm to about 2,000 µm, from about 450 µm to about 2,000 µm, from about 550 µm to about 2,000 µm, from about 650 µm to about 2,000 µm, from about 750 µm to about 2,000 µm, from about 850 µm to about 2,000 µm, from about 950 µm to about 2,000 µm, from about 1050 µm to about 2,000 µm, from about 1150 µm to about 2,000 µm, from about 1250 µm to about 2,000 µm, from about 1350 µm to about 2,000 µm, from about 1450 µm to about 2,000 µm, from about 1550 µm to about 2,000 µm, from about 10 µm to about 1,900 µm, from about 10 µm to about 1,800 µm, from about 10 µm to about 1,700 µm, from about 10 µm to about 1,600 µm, from about 10 µm to about 1,500 µm, from about 10 µm to about 1,400 µm, from about 10 µm to about 1,300 µm, from about 10 µm to about 1,200 µm, from about 10 µm to about 1,100 µm, from about 10 µm to about 1,000 µm, from about 10 µm to about 900 µm, from about 10 µm to about 800 µm, from about 10 µm to about 700 µm, from about 10 µm to about 600 µm, from about 10 µm to about 500 µm, from about 10 µm to about 400 µm, from about 10 µm to about 300 µm, from about 10 µm to about 200 µm, or from about 10 µm to about 100 µm, but may not be limited thereto.

In an embodiment of the present disclosure, an outer shape of the cross section of the microneedle shape may be polygonal and/or curved, but may not be limited thereto. For example, the cross section of the microneedle shape may have one selected from the group consisting of a triangular shape, a tetragonal shape, a pentagonal shape, a hexagonal shape, a circular shape, a semicircular shape, an oval shape, a fan shape, and combinations thereof.

Figure 3A:
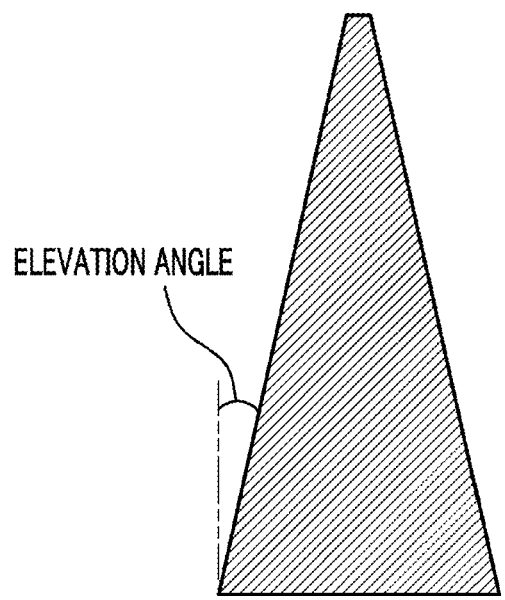
FIG. 3A is a plan view of a microneedle shape of the microneedle template according to an embodiment of the present disclosure.
Figure 3B:
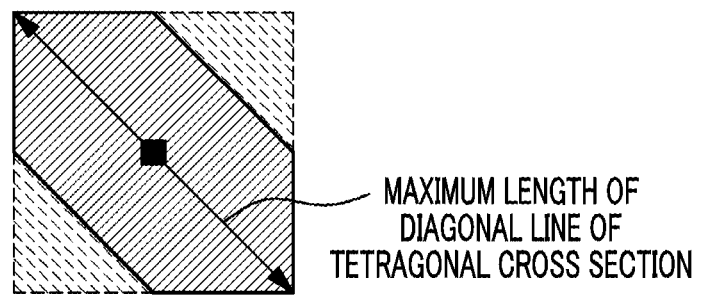
FIG. 3B is the cross section of the microneedle shape has a tetragonal shape.
Figure 4A:
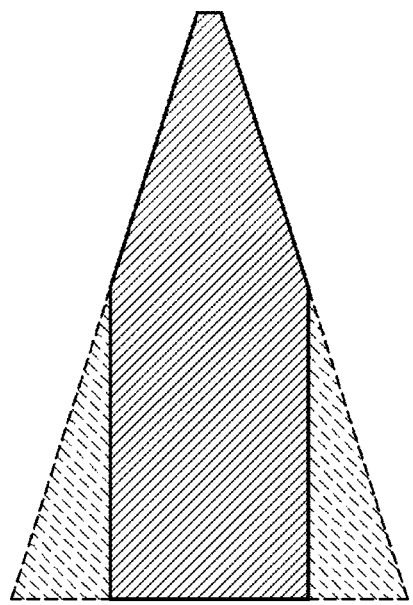
FIG. 4A is a plan view of a microneedle shape of the microneedle template according to an embodiment of the present disclosure.
Figure 4B:
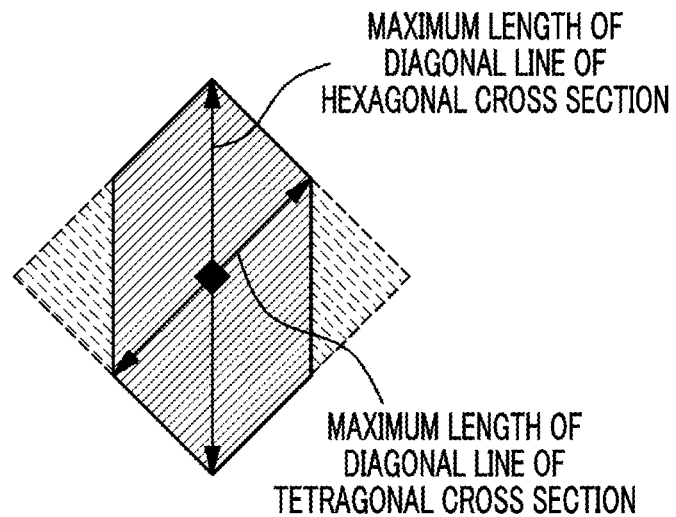
FIG. 4B is the cross section of the microneedle shape has a combination of a tetragonal shape and a hexagonal shape.

In an embodiment of the present disclosure, the cross section of the microneedle shape may have a tetragonal shape only (FIGS. 3A and 3B), or may have a combination of a tetragonal shape and a hexagonal shape (FIGS. 4A and 4B).

In an embodiment of the present disclosure, when the cross section of the microneedle shape has a tetragonal shape only, the maximum length of a diagonal line of the tetragonal cross section may be from about 100 µm to about 1,000 µm, as shown in FIGS. 3A and 3B. For example, when the maximum length of the diagonal line of the tetragonal cross section is less than about 100 µm, a microneedle prepared using the microneedle template may be bent when penetrating the stratum corneum of the skin. For example, when the maximum length of the diagonal line of the tetragonal cross section is above about 1,000 µm, the height of the microneedle prepared using the microneedle template may increase, which may cause pain to the skin.

In an embodiment of the present disclosure, if the cross section of the microneedle shape has a tetragonal shape only, the microneedle shape may have an elevation angle of from about 20° to about 60° as shown in FIGS. 3A and 3B, but may not be limited thereto. For example, when the microneedle shape has the elevation angle of less than 20°, the height of the microneedle may increase, which may cause pain to the skin. For example, the microneedle shape has an elevation angle of above 60°, the skin penetration ratio of the microneedle prepared using the microneedle template may decrease.

In an embodiment of the present disclosure, when the cross section of the each microneedle shape includes a combination of a tetragonal shape and a hexagonal shape, a portion having the hexagonal cross section may be located at which the microneedle shape is in contact with the substrate and a portion having the tetragonal cross section may be located at the end of the microneedle shape in a direction where the microneedle shape is in contact with the skin, as shown in FIGS. 4A and 4B. When the cross section of the microneedle shape has the combination of a tetragonal shape and a hexagonal shape, a resistance of the skin to the microneedle relatively decreases, and thus the microneedle can penetrate the skin better. However, the present disclosure may not be limited thereto.

In an embodiment of the present disclosure, in the each microneedle shape, a ratio of the length of the portion having the hexagonal cross section to the length of the portion having the tetragonal cross section may be from about 1:0.1 to about 1:2, but may not be limited thereto (FIGS. 4A and 4B).

In an embodiment of the present disclosure, if the ratio is less than the above-described range, the tip end of the microneedle prepared using the microneedle template may be bent or broken when penetrating the skin.

In an embodiment of the present disclosure, if the ratio is above the above-described range, the portion having the hexagonal cross section of the microneedle prepared using the microneedle template may not penetrate the stratum corneum of the skin.

In an embodiment of the present disclosure, in the each microneedle shape, a ratio of the maximum length of a diagonal line of the tetragonal cross section to the maximum length of a diagonal line of the hexagonal cross section may be from about 1:2 to about 1:10 (FIGS. 4A and 4B).

In an embodiment of the present disclosure, if the ratio is less than the above-described range, the portion having the hexagonal cross section of the microneedle prepared using the microneedle template may not penetrate the stratum corneum of the skin. However, the present disclosure may not be limited thereto.

In an embodiment of the present disclosure, if the ratio is above the above-described range, the tip end of the microneedle prepared using the microneedle template may be bent or broken when penetrating the skin, but may not be limited thereto.

A second aspect of the present disclosure provides a method for preparing a microneedle template, including: forming at least one microneedle shapes on a substrate; and forming a diamond layer on the surface of the at least one microneedle shapes.

Detailed descriptions on the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, the substrate may include one selected from the group consisting of a metal, a semimetal, an alloy, a semimetal compound, a metal compound, and combinations thereof.

In an embodiment of the present disclosure, the metal may include one selected from the group consisting of tungsten, titanium, molybdenum, niobium, tantalum, chromium, and combinations thereof, but may not be limited thereto.

In an embodiment of the present disclosure, the semimetal may include one selected from the group consisting of silicon, germanium, arsenic, antimony, tellurium, polonium, and combinations thereof, but may not be limited thereto.

In an embodiment of the present disclosure, the alloy may include an ultrahard alloy, and the ultrahard alloy may include one selected from the group consisting of the combinations of carbides of metals in Groups IVB, VB, VIB of the Periodic Table of Elements, such as WC, TiC, MoC, NbC, TaC, $Cr_3C_2$, and the like, but may not be limited thereto.

In an embodiment of the present disclosure, the ultrahard alloy may be given electrical conductivity by using a palladium catalyst, but may not be limited thereto. When the electrical conductivity is given using the palladium catalyst, well-known materials such as a conduction agent used for plating on an ABS resin or the like may be used. However, the present disclosure may not be limited thereto.

In an embodiment of the present disclosure, the semimetal compound may include one selected from the group consisting of a silicon nitride, a silicon carbide, silicon oxide, and combinations thereof, but may not be limited thereto. Ceramic including the silicon nitride, the silicon carbide, the silicon oxide, and the like has excellent thermal shock resistance and high rupture resistance and thus can improve processability and durability such as thermal resistance and wear resistance of the microneedle template. Therefore, the microneedle template according to an embodiment of the present disclosure can be used properly for mass production of microneedles.

In an embodiment of the present disclosure, the metal compound may include a compound of the metal, but may not be limited thereto. The metal compound may include, for example, one selected from the group consisting of an oxide, a nitride, a carbide, an oxynitride and a carbonitride of the metal, and combinations thereof, but may not be limited thereto.

In an embodiment of the present disclosure, the substrate may be ground using a tool, such as a diamond-coated wheel, capable of grinding a metal such as an ultrahard alloy, but may not be limited thereto.

In an embodiment of the present disclosure, the diamond layer may be formed by a chemical vapor deposition method or an atomic layer deposition method, but may not be limited thereto. The chemical vapor deposition method may include, for example, a chemical vapor deposition method using DC plasma, a chemical vapor deposition method using RF plasma, a chemical vapor deposition method using a hot filament, a chemical vapor deposition method using microwave plasma, and a chemical vapor deposition method using electron cyclotron resonance (ECR) plasma, but may not be limited thereto.

In an embodiment of the present disclosure, the diamond layer may be deposited by the chemical vapor deposition method at a very high temperature, and the diamond layer may make the microneedle template more uniformly by coating on an uneven surface formed during a grinding process of the substrate on which the at least one microneedle shapes is formed.

A third aspect of the present disclosure provides a method for preparing a microneedle, including: forming a negative mold using a microneedle template according to the first aspect of the present disclosure; and adding a microneedle-forming material to the negative mold and removing the negative mold to obtain a microneedle.

Detailed descriptions on the third aspect of the present disclosure, which overlap with those of the first and second aspects of the present disclosure, are omitted hereinafter, but the descriptions of the first and second aspects of the present disclosure may be identically applied to the third aspect of the present disclosure, even though they are omitted hereinafter.

In an embodiment of the present disclosure, the forming the negative mold may include applying a templating material to the microneedle template, or immersing the microneedle template into the templating material.

In an embodiment of the present disclosure, the templating material may include one selected from the group consisting of silicon, a metal, a polymer, and combinations thereof, but may not be limited thereto. For example, the polymer may be a curable polymer (resin), a silicone-based polymer, or an elastic polymer, but may not be limited thereto. For example, the curable polymer (resin) may include styrene-butadiene-styrene (SBS), epoxy resin, or phenol resin, but may not be limited thereto. For example, the silicon-based polymer may include polydimethylsiloxane (PDMS) or the like, but may not be limited thereto. The elastic polymer may be polyurethane, but may not be limited thereto.

In an embodiment of the present disclosure, the microneedle may be formed of a well-known microneedle-forming material, but may not be limited thereto. The microneedle-forming material may include one selected from the group consisting of materials dissolved in the body, metals, polymers, silicon, and combinations thereof, but may not be limited thereto.

In an embodiment of the present disclosure, the materials dissolved in the body may include, e.g., a hyaluronic acid, a salt of hyaluronic acid, a cellulose, a vinylpyrrolidone-vinyl acetate copolymer, a polyvinyl alcohol, a polyvinyl pyrrolidone, a saccharide, or mixture thereof, but may not be limited thereto.

In an embodiment of the present disclosure, the cellulose may include a cellulose polymer, a microfibrillated cellulose, hydroxypropyl methylcellulose, a hydroxyalkyl cellulose, hydroxyethyl cellulose, hydroxypropyl cellulose, ethyl hydroxyethyl cellulose, an alkyl cellulose, carboxymethyl cellulose, hydroxypropyl methylcellulose, sodium carboxymethylcellulose, or mixture thereof, but may not be limited thereto.

In an embodiment of the present disclosure, the saccharide may include xylose, sucrose, maltose, lactose, trehalose, dextran, starch, or mixture thereof, but may not be limited thereto.

In an embodiment of the present disclosure, the microneedle-forming material may further include a material selected from the group consisting of a viscous material, a biodegradable material, a drug, and combinations thereof, but may not be limited thereto.

In an embodiment of the present disclosure, the viscous material may include one selected from the group consisting of a polyvinyl pyrrolidone, a dextran, a gelatin, a glycerin, a polyethylene glycol, a polysorbate, a propylene glycol, a povidone, a carbomer, a gum ghatti, a guar gum, a glucomannan, glucosamine, a dammer resin, rennet casein, locust bean gum, psyllium seed gum, xanthan gum, arabinogalactan, arabic gum, alginic acid, gellan gum, carrageenan, karaya gum, curdlan, chitosan, chitin, tara gum, tamarind gum, tragacanth gum, furcelleran, pectin, pullulan, and combinations thereof, but may not be limited thereto.

In an embodiment of the present disclosure, the drug may include physiologically active peptides and derivatives thereof, a nucleic acid, an oligonucleotide, various antigenic proteins, bacteria, a virus fragment, and the like, but may not be limited thereto. The physiologically active peptides and derivatives thereof may include, e.g., calcitonin, adrenocorticotropic hormone, parathyroid hormone (PTH), hPTH (1→34), insulin, exendin, secretin, oxytocin, angiotensin, β-endorphin, glucagon, vasopressin, somatostatin, gastrin, luteinizing hormone, releasing hormones, enkephalin, neurotensin, atrial natriuretic peptide, growth hormone, growth hormone releasing hormone, bradykinin, substance P, dynorphin, thyroid stimulating hormone, prolactin, interferon, interleukin, G-CSF, glutathione peroxidase, superoxide dismutase, desmopressin, somatomedin, endothelin, and salts thereof. The antigenic proteins may include one selected from the group consisting of influenza antigens, HBs surface antigens, HBe antigens, and combinations thereof, but may not be limited thereto.

In an embodiment of the present disclosure, the microneedle-forming material may further include a plasticizer, a surfactant, a preservative, an antiphlogistic agent, and the like, but may not be limited thereto.

A fourth aspect of the present disclosure provides a microneedle, prepared by the method for preparing a microneedle.

Detailed descriptions on the fourth aspect of the present disclosure, which overlap with those of the first, second, and third aspects of the present disclosure, are omitted hereinafter, but the descriptions of the first, second, and third aspects of the present disclosure may be identically applied to the fourth aspect of the present disclosure, even though they are omitted hereinafter.

In an embodiment of the present disclosure, the length of the microneedle shape may be suitable to penetrate the stratum corneum of the skin and reach the surface layer or dermal layer under the stratum corneum and may be, for example, about 2,000 μm or less, from about 10 μm to about 2,000 μm, from about 150 μm to about 2,000 μm, from about 250 μm to about 2,000 μm, from about 350 μm to about 2,000 μm, from about 450 μm to about 2,000 μm, from about 550 μm to about 2,000 μm, from about 650 μm to about 2,000 μm, from about 750 μm to about 2,000 μm, from about 850 μm to about 2,000 μm, from about 950 μm to about 2,000 μm, from about 1050 μm to about 2,000 μm, from about 1150 μm to about 2,000 μm, from about 1250 μm to about 2,000 μm, from about 1350 μm to about 2,000 μm, from about 1450 μm to about 2,000 μm, from about 1550 μm to about 2,000 μm, from about 10 μm to about 1,900 μm, from about 10 μm to about 1,800 μm, from about 10 μm to about 1,700 μm, from about 10 μm to about 1,600 μm, from about 10 μm to about 1,500 μm, from about 10 μm to about 1,400 μm, from about 10 μm to about 1,300 μm, from about 10 μm to about 1,200 μm, from about 10 μm to about 1,100 μm, from about 10 μm to about 1,000 μm, from about 10 μm to about 900 μm, from about 10 μm to about 800 μm, from about 10 μm to about 700 μm, from about 10 μm to about 600 μm, from about 10 μm to about 500 μm, from about 10 μm to about 400 μm, from about 10 μm to about 300 μm, from about 10 μm to about 200 μm, or from about 10 μm to about 100 μm, but may not be limited thereto.

In an embodiment of the present disclosure, an outer shape of the cross section of the microneedle may be polygonal and/or curved, but may not be limited thereto. For example, the cross section of the microneedle may have one selected from the group consisting of a triangular shape, a tetragonal shape, a pentagonal shape, a hexagonal shape, a circular shape, a semicircular shape, an oval shape, a fan shape, and combinations thereof. In an embodiment of the present disclosure, the cross section of the microneedle may have a tetragonal shape only, or may have a combination of a tetragonal shape and a hexagonal shape.

In an embodiment of the present disclosure, when the cross section of the each microneedle includes a combination of a tetragonal shape and a hexagonal shape, a portion having the hexagonal cross section may be located at which the microneedle is in contact with the substrate and a portion having the tetragonal cross section may be located at the end of the microneedle in a direction where the microneedle shape is in contact with the skin, as shown in FIGS. 4A and 4B. When the cross section of the microneedle has the combination of a tetragonal shape and a hexagonal shape, a resistance of the skin to the microneedle relatively decreases, and thus the microneedle can penetrate the skin better.

In an embodiment of the present disclosure, in the each microneedle, a ratio of the length of the portion having the hexagonal cross section to the length of the portion having the tetragonal cross section may be from about 1:0.1 to about 1:2 (FIGS. 4A and 4B).

In an embodiment of the present disclosure, if the ratio is less than the above-described range, the tip end of the microneedle may be bent or broken when penetrating the skin. In an embodiment of the present disclosure, if the ratio is above the above-described range, the portion having the hexagonal cross section of the microneedle may not penetrate the stratum corneum of the skin.

In an embodiment of the present disclosure, the microneedle may contain a well-known microneedle-forming material. The microneedle may contain one selected from the group consisting of materials dissolved in the body, metals, polymers, silicone, and combinations thereof, but may not be limited thereto.

In an embodiment of the present disclosure, the materials dissolved in the body may include, e.g., a hyaluronic acid, a salt of hyaluronic acid, a cellulose, a vinylpyrrolidone-vinyl acetate copolymer, a polyvinyl alcohol, a polyvinyl pyrrolidone, a saccharide, or mixture thereof, but may not be limited thereto.

In an embodiment of the present disclosure, the cellulose may include a cellulose polymer, a microfibrillated cellulose, hydroxypropyl methylcellulose, a hydroxyalkyl cellulose, hydroxyethyl cellulose, hydroxypropyl cellulose, ethyl hydroxyethyl cellulose, an alkyl cellulose, carboxymethyl cellulose, hydroxypropyl methylcellulose, sodium carboxymethylcellulose, or mixture thereof, but may not be limited thereto.

In an embodiment of the present disclosure, the saccharide may include xylose, sucrose, maltose, lactose, trehalose, dextran, starch, or mixture thereof, but may not be limited thereto.

In an embodiment of the present disclosure, the microneedle may further contain a material selected from the group consisting of a viscous material, a biodegradable material, a drug, and combinations thereof, but may not be limited thereto.

In an embodiment of the present disclosure, the viscous material may include one selected from the group consisting of a polyvinyl pyrrolidone, a dextran, a gelatin, a glycerin, a polyethylene glycol, a polysorbate, a propylene glycol, a povidone, a carbomer, a gum ghatti, a guar gum, a glucomannan, glucosamine, a dammer resin, rennet casein, locust bean gum, psyllium seed gum, xanthan gum, arabinogalactan, arabic gum, alginic acid, gellan gum, carrageenan, karaya gum, curdlan, chitosan, chitin, tara gum, tamarind gum, tragacanth gum, furcelleran, pectin, pullulan, and combinations thereof, but may not be limited thereto.

In an embodiment of the present disclosure, the drug may include physiologically active peptides and derivatives thereof, a nucleic acid, an oligonucleotide, various antigenic proteins, bacteria, a virus fragment, and the like, but may not be limited thereto. The physiologically active peptides and derivatives thereof may include, e.g., calcitonin, adrenocorticotropic hormone, parathyroid hormone (PTH), hPTH (1→34), insulin, exendin, secretin, oxytocin, angiotensin, β-endorphin, glucagon, vasopressin, somatostatin, gastrin, luteinizing hormone, releasing hormones, enkephalin, neurotensin, atrial natriuretic peptide, growth hormone, growth hormone releasing hormone, bradykinin, substance P, dynorphin, thyroid stimulating hormone, prolactin, interferon, interleukin, G-CSF, glutathione peroxidase, superoxide dismutase, desmopressin, somatomedin, endothelin, and salts thereof. The antigenic proteins may include one selected from the group consisting of influenza antigens, HBs surface antigens, HBe antigens, and combinations thereof, but may not be limited thereto.

In an embodiment of the present disclosure, the microneedle may further contain a plasticizer, a surfactant, a preservative, an antiphlogistic agent, and the like, but may not be limited thereto.

In an embodiment of the present disclosure, the microneedle is prepared using a microneedle template having a smooth surface with a peculiar shape and thus has high skin penetration ratio and can efficiently deliver a material into the body.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

Example 1: Preparation of Microneedle Template

Figure 5A:
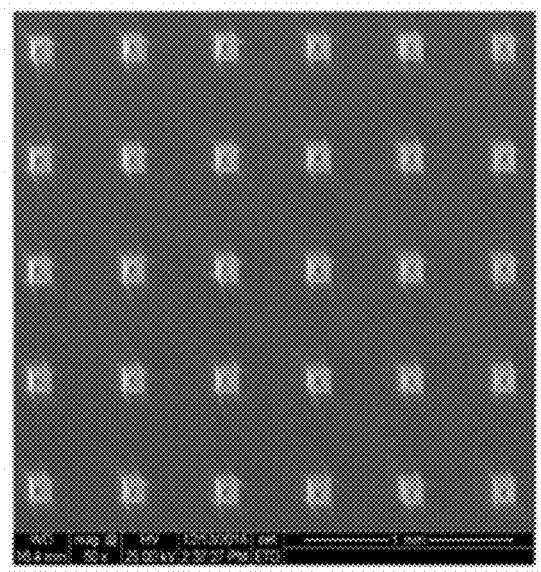
FIGS. 5A to 5C show photographs of a microneedle template according to an example of the present disclosure, and the cross section of the microneedle shape has a tetragonal shape.
Figure 5B:
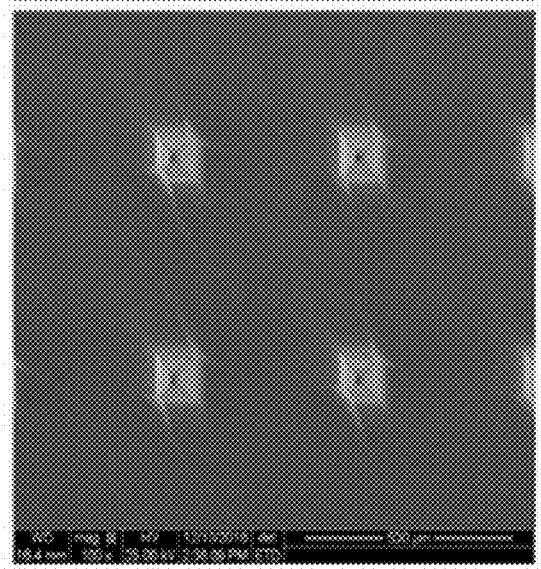
Figure 5C:
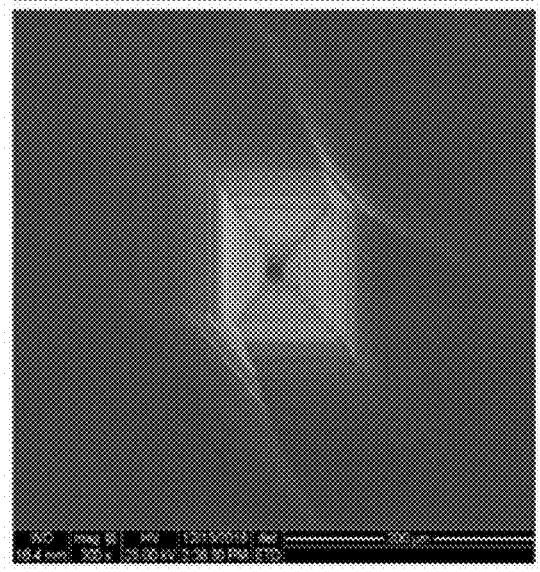

A tungsten carbide substrate was ground with a diamond-coated wheel to form a microneedle shape on the substrate (First grinding). After the first grinding, the cross section of the microneedle shape had a tetragonal shape only, as shown in FIGS. 5A to 5C.

Then, the microneedle shape was further ground with a diamond wheel, and thus the microneedle shape had a portion having a tetragonal cross section and a portion having a hexagonal cross section, as shown in FIGS. 6A to 6C and FIGS. 7A and 7B (Second grinding).

After the first grinding and the second grinding, a microneedle template was pre-treated to remove foreign materials from the surface and then washed to well form a diamond layer on the surface of the microneedle shape.

Then, after the first grinding and the second grinding, each microneedle template was located in a CVD coating chamber having an internal temperature of about 2,000° C., diamond was deposited to a thickness of 1 μm to 3 μm on the surface of the microneedle shape by a chemical vapor deposition method using a diamond filament.

Example 2: Preparation of Microneedle

The microneedle template according to Example 1 was applied with PDMS or silicone or immersed in PDMS or silicone to form a negative mold.

The negative mold was applied with a mixture of 5% hyaluronic acid MMW, 3% hyaluronic acid oligomer, 0.5% trehalose, and 1% collagen without blisters.

Then, the mixture was dried at 50° C. for 3 hours to form a microneedle, and the microneedle was separated from the negative mold.

Figure 7A:
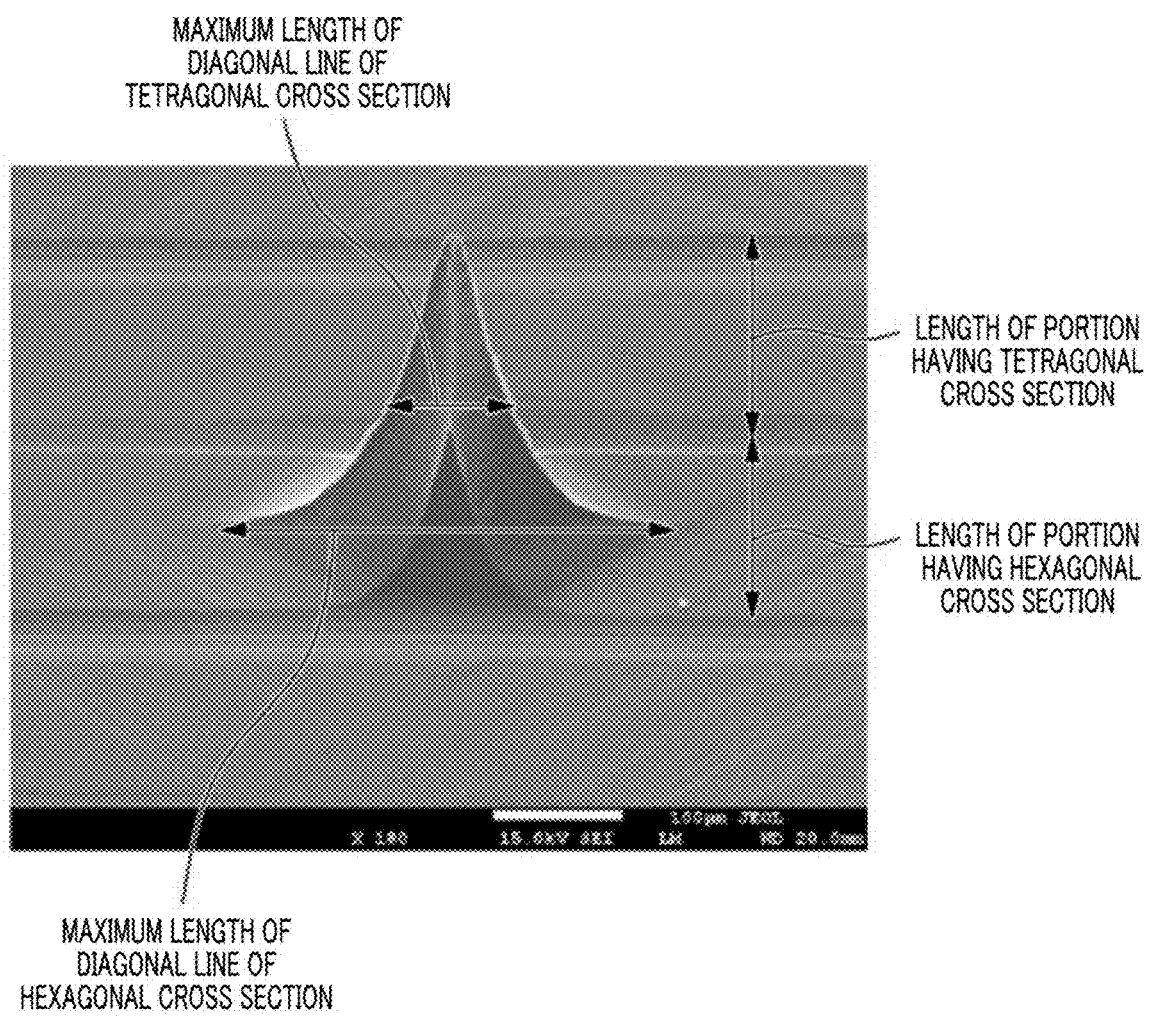
FIG. 7A is a photograph of a microneedle according to an example of the present disclosure.
Figure 7B:
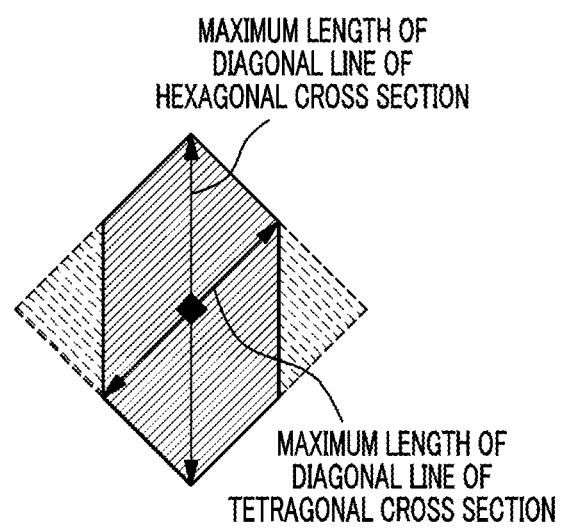
FIG. 7B is the cross section of the microneedle shape has a combination of a tetragonal shape and a hexagonal shape.

The shape of the obtained microneedle was as shown in FIGS. 7A and 7B. A ratio of the length of a portion having a hexagonal cross section to the length of a portion having a tetragonal cross section of the microneedle was measured at 1:1, and a ratio of the maximum length (67 μm) of a diagonal line of the tetragonal cross section to the maximum length (351 μm) of a diagonal line of the hexagonal cross section was measured at 1:5.23.

Test Example 1: Skin Penetrating Rate Test of Microneedle

A microneedle patch in which the number of microneedles according to Example 2 is 10×10 (100 microneedles in total) was dried in a 700° C. oven to remove remaining moisture.

The microneedle patch from which remaining moisture was removed was placed on the skin of the back of a pig and then pressed with weight of 3 kg for 10 seconds. Then, the microneedle patch was removed from the skin of the back of the pig.

Figure 6A:
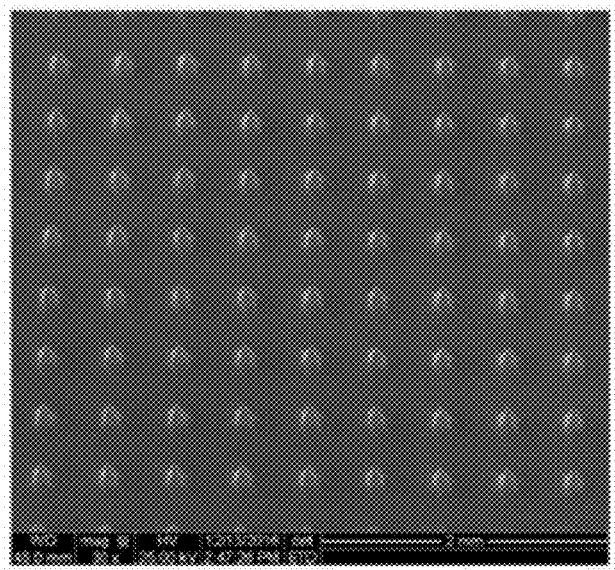
FIGS. 6A to 6C show photographs of a microneedle template according to an example of the present disclosure, and the cross section of the microneedle shape has a combination of a tetragonal shape and a hexagonal shape.
Figure 6B:
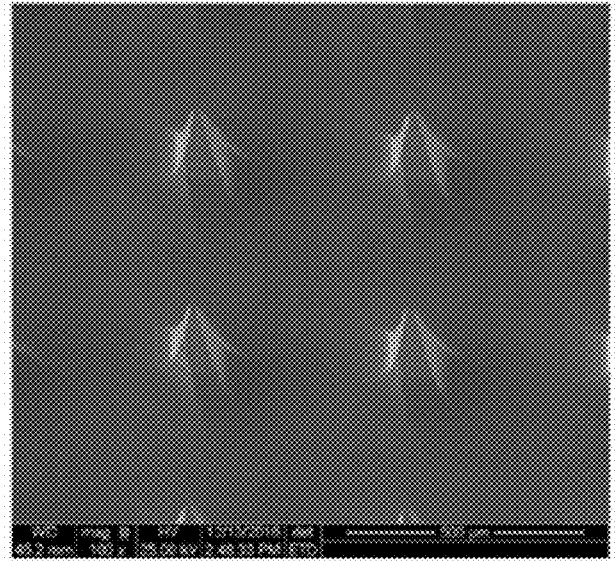
Figure 6C:
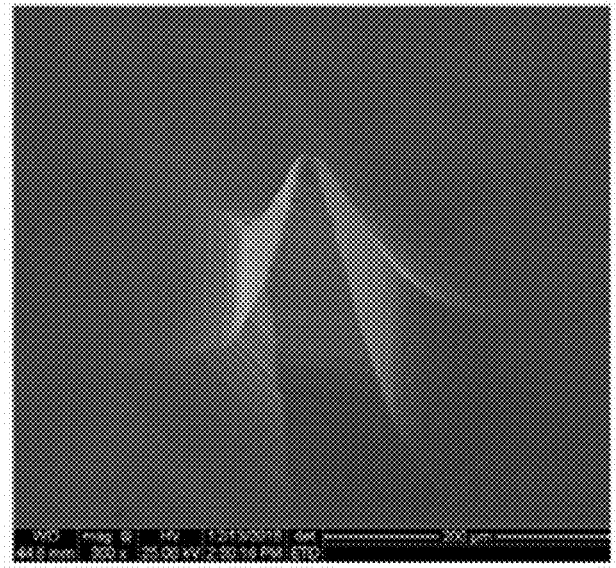
Figure 8:
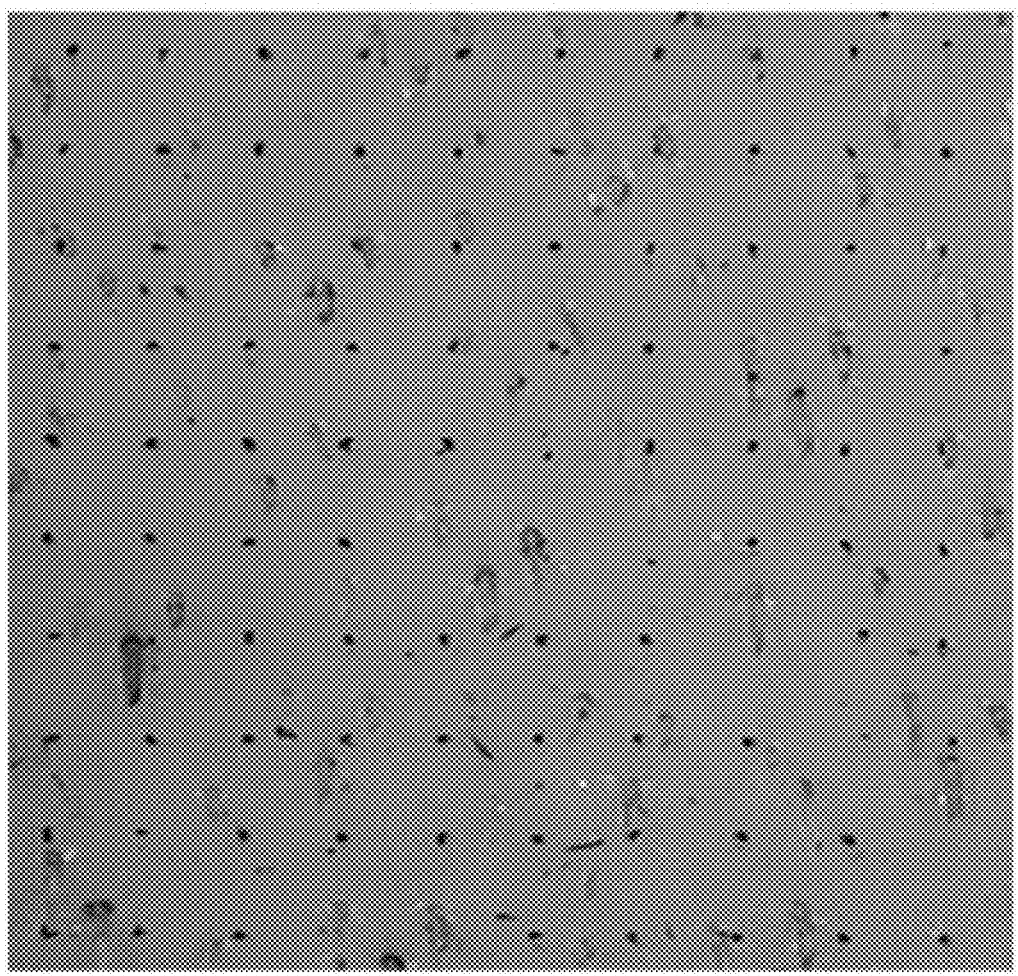
FIG. 8 is a photograph showing the result of skin penetration test of a microneedle according to an example of the present disclosure.

Thereafter, the skin of the back of the pig was applied with trypan blue to dye the dermal layer of the skin of the back of the pig. Then, the skin of the back of the pig was observed through a microscope. The dyeing result and penetrating rate were as shown in FIG. 6A to 6C. As shown in FIG. 8, 97.5 holes in the skin of the back of the pig was dyed. Thus, it can be seen that the prepared microneedles has excellent skin penetrating rate of about 97.5%.

Test Example 2: Skin Penetrating Rate and Solubility Test of Microneedle

The skin penetrating rate and solubility of the two kinds of microneedles prepared using the microneedle templates obtained by the first grinding and the second grinding, respectively, according to Example 1 were tested.

Figure 9:
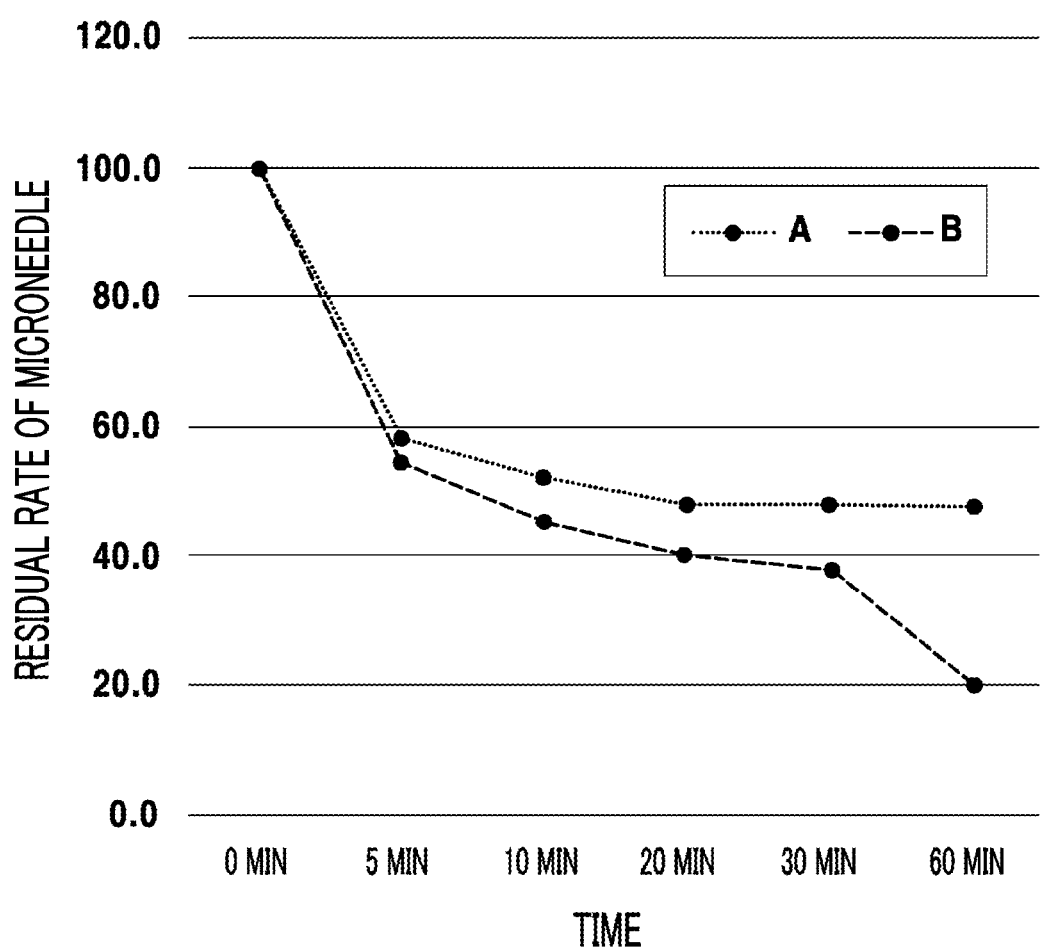
FIG. 9 is a graph showing the result of skin penetration and solubility test of a microneedle according to an example of the present disclosure.

First, the initial lengths of the two kinds of microneedles and the lengths of the microneedles pulled out from the skin of a pig after a predetermined time after the microneedles were stuck into the skin of the pig were measured using a microscope, as shown in FIG. 9 and Table 1.

In FIG. 9 and Table 1, A and B denote the microneedles prepared using the microneedle templates obtained after the first grinding and the second grinding, respectively. The horizontal axis in FIG. 9 represents the time during which the microneedles were stuck to the skin of the pig, and the vertical axis represents the lengths of the microneedles. In Table 1, a residual rate (%) represents a ratio of the length of B relative to the length of A.

As shown in FIG. 8 and Table 1, the microneedle prepared using the microneedle template obtained after the second grinding exhibited excellent skin penetrating rate and solubility compared to the microneedle prepared using the microneedle template obtained by the first grinding. In view of the fact that A had a residual rate of 47.6% after 60 minutes, and B had a residual rate of 19.7% after 60 minutes, it could be seen that the microneedle prepared using the microneedle template obtained after the second grinding more deeply penetrated the skin and was better dissolved in the skin.

TABLE 1

|  | Time | | | | | |
| --- | --- | --- | --- | --- | --- | --- |
|  | 0 min | 5 min | 10 min | 20 min | 30 min | 60 min |
| Residual rate (%) of A | 100.0 | 58.0 | 52.0 | 47.8 | 48.0 | 47.6 |
| Residual rate (%) of B | 100.0 | 54.8 | 45.2 | 39.4 | 37.9 | 19.7 |

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A microneedle template, comprising:
a substrate on which at least one microneedle shape is formed; and
a diamond layer formed on the surface of the at least one microneedle shape,
wherein a thickness of the diamond layer is 10 μm or less,
wherein the cross section of each of the at least one microneedle shapes consists of a combination of a tetragonal shape and a hexagonal shape,
wherein a portion having the hexagonal cross section is located where the at least one microneedle shape is in contact with the substrate and a portion having the tetragonal cross section is located at the end of the at least one microneedle shape,
wherein, in each of the at least one microneedle shapes, a ratio of the length of the portion having the hexagonal cross section to the length of the portion having the tetragonal cross section is from 1:0.1 to 1:2, and in each of the at least one microneedle shapes, the length of the microneedle shape consists of the length of the portion having the hexagonal cross section and the length of the portion having the tetragonal cross section, and
wherein, in each of the at least one microneedle shapes, a ratio of the maximum length of a diagonal line of the tetragonal cross section to the maximum length of a diagonal line of the hexagonal cross section is from 1:2 to 1:10.

2. The microneedle template of claim 1,
wherein the substrate includes one selected from the group consisting of a metal, an alloy, a semimetal compound, a metal compound, and combinations thereof,
wherein the metal includes one selected from the group consisting of tungsten, titanium, molybdenum, niobium, tantalum, chromium, and combinations thereof,
wherein the alloy includes one selected from the group consisting of WC, TiC, MoC, NbC, TaC, $Cr_3C_2$, and combinations thereof,
wherein the semimetal compound includes one selected from the group consisting of a silicon nitride, a silicon carbide, a silicon oxide, and combinations thereof, and
wherein the metal compound includes one selected from the group consisting of an oxide, a nitride, a carbide, an oxynitride, and a carbonitride of the metal, and combinations thereof.

3. The microneedle template of claim 1, wherein a length of the at least one microneedle shape is 2,000 μm or less.

4. A method for preparing a microneedle template, comprising:
forming at least one microneedle shape on a substrate; and
forming a diamond layer on the surface of the at least one microneedle shape,
wherein a thickness of the diamond layer is 10 μm or less,
wherein the cross section of each of the at least one microneedle shapes consisting of a combination of a tetragonal shape and a hexagonal shape,
wherein a portion having the hexagonal cross section is located where the at least one microneedle shape is in contact with the substrate and a portion having the tetragonal cross section is located at the end of the microneedle shape,
wherein, in each of the at least one microneedle shapes, a ratio of the length of the portion having the hexagonal cross section to the length of the portion having the tetragonal cross section is from 1:0.1 to 1:2, and in each of the at least one microneedle shapes, the length of the microneedle shape consists of the length of the portion having the hexagonal cross section and the length of the portion having the tetragonal cross section, and
wherein, in each of the at least one microneedle shapes, a ratio of the maximum length of a diagonal line of the tetragonal cross section to the maximum length of a diagonal line of the hexagonal cross section is from 1:2 to 1:10.

5. The method for preparing a microneedle template of claim 4,
wherein the substrate includes one selected from the group consisting of a metal, an alloy, a semimetal compound, a metal compound, and combinations thereof,
wherein the metal includes one selected from the group consisting of tungsten, titanium, molybdenum, niobium, tantalum, chromium, and combinations thereof,
wherein the alloy includes one selected from the group consisting of WC, TiC, MoC, NbC, TaC, $Cr_3C_2$, and combinations thereof,
wherein the semimetal compound includes one selected from the group consisting of a silicon nitride, a silicon carbide, a silicon oxide, and combinations thereof, and
wherein the metal compound includes one selected from the group consisting of an oxide, a nitride, a carbide, an oxynitride, and a carbonitride of the metal, and combinations thereof.

6. The method for preparing a microneedle template of claim 4, wherein the diamond layer is formed by a chemical vapor deposition method or an atomic layer deposition method.

7. A method for preparing a microneedle, comprising:
forming a negative mold using the microneedle template according to claim 1; and
adding a microneedle-forming material to the negative mold and removing the negative mold to obtain a microneedle,
wherein the cross section of the microneedle consists of a combination of a tetragonal shape and a hexagonal shape,
wherein a portion having the hexagonal cross section is located where the microneedle is in contact with the substrate and a portion having the tetragonal cross section is located at the end of the microneedle,
wherein, in the microneedle, a ratio of the length of the portion having the hexagonal cross section to the length of the portion having the tetragonal cross section is from 1:0.1 to 1:2, and in the microneedle, the length of the microneedle consists of the length of the Portion having the hexagonal cross section and the length of the portion having the tetragonal cross section, and
wherein, in the microneedle, a ratio of the maximum length of a diagonal line of the tetragonal cross section to the maximum length of a diagonal line of the hexagonal cross section is from 1:2 to 1:10.

8. The method for preparing a microneedle of claim 7, wherein the forming the negative mold includes applying a templating material to the microneedle template, or immersing the microneedle template into the templating material.

9. The method for preparing a microneedle of claim 8, wherein the templating material includes one selected from the group consisting of a silicon, a metal, a polymer, and combinations thereof.

10. The method for preparing a microneedle of claim 7, wherein the microneedle-forming material further includes a material selected from the group consisting of a viscous material, a drug, and combinations thereof.

11. A microneedle, prepared using a microneedle template according to claim 1,
wherein the cross section of the microneedle consists of a combination of a tetragonal shape and a hexagonal shape,
wherein a portion having the hexagonal cross section is located where the microneedle is in contact with the substrate and a portion having the tetragonal cross section is located at the end of the microneedle in a direction where the microneedle is in contact with a skin,
wherein, in the microneedle, a ratio of the length of the portion having the hexagonal cross section to the length of the portion having the tetragonal cross section is from 1:0.1 to 1:2, the length of the microneedle consists of the length of the Portion having the hexagonal cross section and the length of the Portion having the tetragonal cross section,
wherein, in the microneedle, a ratio of the maximum length of a diagonal line of the tetragonal cross section to the maximum length of a diagonal line of the hexagonal cross section is from 1:2 to 1:10, and
wherein, as the cross section of the microneedle consists of the combination of the tetragonal shape and the hexagonal shape, a resistance of the skin to the microneedle decreases so that a skin penetrating rate of the microneedle is increased.

* * * * *